United States Patent [19]

Kawabuchi et al.

[11] Patent Number: 5,070,734
[45] Date of Patent: Dec. 10, 1991

[54] ULTRASONIC DIAGNOSTIC APPARATUS

[75] Inventors: Masami Kawabuchi; Yukuo Sakagaito, both of Yokohama; Akitoshi Mori, Kawasaki, all of Japan

[73] Assignee: Matsushita Electric Industrial Co., Ltd., Japan

[21] Appl. No.: 365,331

[22] Filed: Jun. 13, 1989

[30] Foreign Application Priority Data

Jun. 15, 1988 [JP] Japan .................. 63-147461
Aug. 23, 1988 [JP] Japan .................. 63-208722

[51] Int. Cl.⁵ ............................................. G01N 29/00
[52] U.S. Cl. ............................................. 73/628
[58] Field of Search .............. 73/628, 621, 633, 618, 73/627, 640, 641

[56] References Cited

U.S. PATENT DOCUMENTS

| 3,898,840 | 8/1975 | McElroy | 73/628 |
| 4,097,835 | 6/1978 | Green | 73/628 |
| 4,413,520 | 11/1983 | Murakami et al. | 73/628 |
| 4,434,661 | 3/1984 | Miwa et al. | 73/628 |
| 4,492,120 | 1/1985 | Lewis et al. | 73/628 |
| 4,530,362 | 7/1985 | Hetz | 73/628 |
| 4,872,346 | 10/1989 | Kelly-Fry et al. | 73/627 |

FOREIGN PATENT DOCUMENTS

0042288 12/1981 European Pat. Off. .
3727213 2/1988 Fed. Rep. of Germany .
61-58648 3/1986 Japan .

Primary Examiner—Hezron E. Williams
Assistant Examiner—Louis M. Arana
Attorney, Agent, or Firm—Lowe, Price, LeBlanc & Becker

[57] ABSTRACT

An ultrasonic diagnostic apparatus comprises at least one piezoelectric transducer which is moved in a scanning process. A first transmission signal and a second transmission signal are different from each other. One of the first and second transmission signals is selectively applied to the transducer. The transducer converts the applied one of the first and second transmission signals into a beam of corresponding ultrasonic wave. The transducer emits the ultrasonic wave beam toward an examined body and receives an echo of the ultrasonic wave beam from the examined body. The transducer converts the received echo into a corresponding received signal. A first signal processor and a second signal processor have different characteristics. The received signal is selectively applied to one of the first and second signal processors to be processed thereby. A sectional image of the examined body is generated on the basis of an output signal from one of the first and second signal processors.

7 Claims, 4 Drawing Sheets

ULTRASONIC DIAGNOSTIC APPARATUS

BACKGROUND OF THE INVENTION

1. Field of the Invention

This invention relates to an ultrasonic diagnostic apparatus of a mechanical-scan type.

2. Description of the Prior Art

Some ultrasonic diagnostic apparatuses of a mechanical-scan type produce a sector sectional image of an examined body. In these prior art apparatuses, during the production of an image of an examined body, a support carrying a set of piezoelectric transducers is moved while a beam of ultrasonic wave is emitted from the transducers toward the examined body and echo signals are received via the transducers.

Japanese published unexamined patent application 61-58648 discloses such a mechanical-scan type ultrasonic diagnostic apparatus. In the apparatus of Japanese patent application 61-58648, when a plurality of images of an examined body for respective different frequencies of ultrasonic waves are required, it is necessary to replace a set of piezoelectric transducers by another set upon each change of the ultrasonic wave frequency from one to another. Thus, it is necessary to previously prepare plurality of sets of piezoelectric transducers having resonance frequencies matching to the respective different frequencies of ultrasonic waves. In addition, the replacement of the transducer set necessitates a portion of a casing accommodating the transducer set to be opened.

SUMMARY OF THE INVENTION

It is an object of this invention to provide a convenient ultrasonic diagnostic apparatus.

A first ultrasonic diagnostic apparatus of this invention comprises at least one piezoelectric transducer; means for moving the transducer in a scanning process; means for generating a first transmission signal; means for generating a second transmission signal different from the first transmission signal; means for selectively applying one of the first and second transmission signals to the transducer, wherein the transducer converts the applied one of the first and second transmission signals into a beam of corresponding ultrasonic wave, wherein the transducer emits the ultrasonic wave beam toward an examined body and receives an echo of the ultrasonic wave beam from the examined body, wherein the transducer converts the received echo into a corresponding received signal; a first signal processor having a characteristic; a second signal processor having a characteristic different from the characteristic of the first signal processor; means for selectively applying the received signal to one of the first and second signal processors to allow said one of the first and second signal processors to process the received signal; and means for generating a sectional image of the examined body on the basis of an output signal from said one of the first and second signal processors.

A second ultrasonic diagnostic apparatus of this invention comprises a piezoelectric transducer; means for moving the transducer in a mechanical scanning process; means for generating a first transmission signal; means for generating a second transmission signal different from the first transmission signal; means for selectively applying one of the first and second transmission signals to the transducer, wherein the transducer converts the applied one of the first and second transmission signals into a beam of corresponding ultrasonic wave, wherein the transducer emits the ultrasonic wave beam toward an examined body and receives an echo of the ultrasonic wave beam from the examined body, and wherein the transducer converts the received echo into a corresponding received signal; and means for generating a sectional image of the examined body on the basis of the received signal.

A third ultrasonic diagnostic apparatus of this invention comprises means for generating a transmission signal; a first piezoelectric transducer converting the transmission signal into a first beam of corresponding ultrasonic wave, the first transducer emitting the first beam toward an examined body and receiving an echo of the first beam from the examined body, the first transducer converting the echo of the first beam into a first received signal, the first transducer having a characteristic; a second piezoelectric transducer converting the transmission signal into a second beam of corresponding ultrasonic wave, the second transducer emitting the second beam toward the examined body and receiving an echo of the second beam from the examined body, the second transducer converting the echo of the second beam into a second received signal, the second transducer having a characteristic different from the characteristic of the first transducer; means for moving the first and second transducers in a mechanical scanning process; means for selectively applying the transmission signal to one of the first and second transducers; means for generating a sectional image of the examined body on the basis of the first received signal; and means for generating a sectional image of the examined body on the basis of the second received signal.

A fourth ultrasonic diagnostic apparatus of this invention comprises means for generating a first transmission signal having a frequency band; means for generating a second transmission signal having a frequency band different from the frequency band of the first transmission signal; a first piezoelectric transducer having a frequency characteristic matching to the frequency band of the first transmission signal, the first transducer converting the first transmission signal into a first beam of corresponding ultrasonic wave, the first transducer emitting the first beam toward an examined body and receiving an echo of the first beam from the examined body, the first transducer converting the echo of the first beam into a first received signal; a second piezoelectric transducer having a frequency characteristic matching to the frequency band of the second transmission signal, the second transducer converting the second transmission signal into a second beam of corresponding ultrasonic wave, the second transducer emitting the second beam toward the examined body and receiving an echo of the second beam from the examined body, the second transducer converting the echo of the second beam into a second received signal; means for moving the first and second transducers in a mechanical scanning process; means for generating a sectional image of the examined body on the basis of the first received signal; means for generating a sectional image of the examined body on the basis of the second received signal; and a casing accommodating the first and second transducers.

DESCRIPTION OF THE FIRST PREFERRED EMBODIMENT

Figure 1:
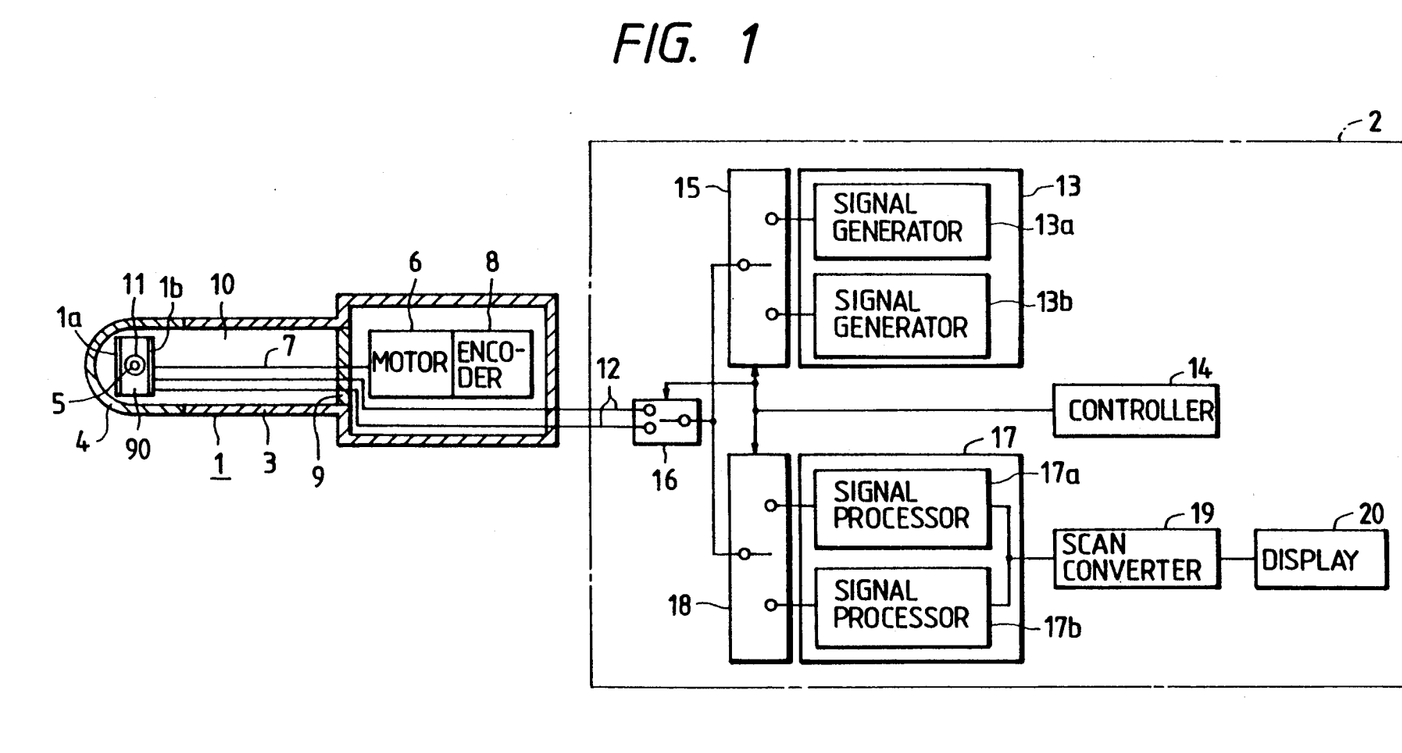
FIG. 1 is a diagram of an ultrasonic diagnostic apparatus according to a first embodiment of this invention.

With reference to FIG. 1, an ultrasonic diagnostic apparatus includes an ultrasonic probe 1 and a main body 2. The ultrasonic probe 1 is of a mechanical-scan type. As will be described hereinafter, the ultrasonic probe 1 is electrically connected to the main body 2.

For example, the ultrasonic probe 1 is designed for use in a colon of an examined body. The ultrasonic probe 1 includes first and second piezoelectric transducers 1a and 1b mounted on opposite surfaces of a rotor 90 respectively. The transducers 1a and 1b have different resonance frequency bands respectively. For example, the centers of the resonance frequency bands of the transducers 1a and 1b are 5 MHz and 7.5 MHz respectively.

The ultrasonic probe 1 has a casing 3 provided with a hemispherical front end which is made of synthetic resin and which forms an acoustic window 4. The rotor 90 is rotatably supported within the acoustic window 4 by a rotary shaft 5. As the rotor 90 rotates, the transducers 1a and 1b are sequentially opposed to the examined body.

The rotor 90 is mechanically coupled via a drive shaft 7 to a motor 6 supported within a rear part of the casing 3. The rotor 90 is driven by the motor 6. An encoder 8 is connected to the motor 6.

A partition wall provided with an oil seal 9 divides the interior of the casing 3 into a front portion and a rear portion accommodating the rotor 90 and the motor 6 respectively. The front portion of the casing 3 is sealingly filled with ultrasonic wave propagation liquid 10 such as water or oil.

The main body 2 feeds and receives transmission signals and reception signals to and from the transducers 1a and 1b via a rotary transformer 11 and signal lines 12. The rotary transformer 11 is supported on the rotor 90 and surrounds the rotary shaft 5. The signal lines 12 extend between the rotary transformer 11 and the main body 2.

The encoder 8 is directly coupled to the drive shaft 7 and generates a signal representing conditions of rotation of the motor 6 and thus representing the positions of the rotor 90 and the transducers 1a and 1b. The output signal from the encoder 8 is transmitted to the main body 2. The main body 2 uses the encoder signal in various controls including control of timings of the transmission and reception of ultrasonic wave.

It should be noted that a drive line to the motor 6, an output line from the encoder 8, and a power supply line to the encoder 8 are omitted from FIG. 1 for clarity.

The main body 2 includes a transmitter 13 having first and second signal generators 13a and 13b. The first generator 13a outputs a first transmission signal having a frequency band whose center equals 5 MHz. The second generator 13b outputs a second transmission signal having a frequency band whose center equals 7.5 MHz. A switch 15 selects one of the first and second transmission signals and passes the selected transmission signal to a switch 16. The switch 16 passes the incoming signal to either the first transducer 1a or the second transducer 1b via the signal lines 12. In other words, the switch 15 functions to select one of the generators 13a and 13b while the switch 16 selects one of the transducers 1a and 1b. The selected generator and the selected transducer are used in the operation of the ultrasonic diagnostic apparatus. The switches 15 and 16 are changed in response to a control signal outputted from a controller 14.

It should be noted that the selection of one of the first and second transmission signals may be responsive to turning on and off of the power supply.

The main body 2 also includes a receiver 17 having first and second signal processors 17a and 17b. The first processor 17a is able to process an echo or reception signal having a frequency band whose center equals 5 MHz. In other words, the first processor 17a has frequency characterisitics matching to a frequency band whose center equals 5 MHz. The second processor 17b is able to process an echo or reception signal having a frequency band whose center equals 7.5 MHz. In other words, the second processor 17b has frequency characteristics matching to a frequency band whose center equals 7.5 MHz. Each of the processors 17a and 17b includes amplifiers, a detector, and various filters in a known way.

It should be noted that the filters in the processors 17a and 17b may include dynamic filters whose center frequencies are subjected to time-dependent variations.

The transducers 1a and 1b convert the first or second transmission signal into a beam of corresponding ultrasonic wave emitted into the examined body. Portions of the emitted ultrasonic beam are reflected within the examined body and return to the transducers 1a and 1b as ultrasonic echoes. The transducers 1a and 1b convert the ultrasonic echoes into first and second received signals which are transmitted to the switch 16 via the rotary transformer 11 and the signal lines 12.

The switch 16 selects one of the first and second received signals and passes the selected received signal to a switch 18. The switch 18 passes the incoming received signal to either the first processor 17a or the second processor 17b. In other words, the switch 18 functions to select one of the processors 17a and 17b. The selected processor is used in the operation of the ultrasonic wave diagnostic apparatus. The switches 16 and 18 are changed in response to the control signal outputted from the controller 14.

Output signals from the processors 17a and 17b are converted by a scan converter 19 into a video signal having a television format. A display 20 generates a sectional image of the examined body in accordance with the video signal outputted from the scan converter 19.

As described previously, the controller 14 controls the switches 15, 16, and 18. The controller 14 may change the switches 15, 16, and 18 at timings determined by the output signal from the encoder 8.

The ultrasonic diagnostic apparatus operates as follows. The motor 6 drives the rotor 90 via the drive shaft 7. Specifically, the rotor 90 with the transducers 1a and 1b are rotated in one direction at a predetermined speed, for example, 600 rpm. One of the first and second transmission signals from the first and second generators 13a and 13b is selected by the switch 15 in response to the control signal from the controller 14. The switch 16 feeds the selected transmission signal to one of the transducers 1a and 1b via the signal line 12 and the rotary transformer 11 in response to the control signal from the controller 14. One of the transducers 1a and 1b converts the fed transmission signal into a beam of corresponding ultrasonic wave and emits the beam toward an examined body.

Echoes of the ultrasonic wave beam are generated at organs of the examined body. The echoes which return to the transducer 1a or 1b are converted into an echo signal or a received signal. The received signal is transmitted to the switch 18 via the rotary transformer 11, the signal line 12, and the switch 16. The switch 18 feeds the received signal to one of the processors 17a and 17b in response to the control signal from the controller 14. One of the processors 17a and 17b processes the received signal. The output signal from one of the processors 17a and 17b is converted by the scan converter 19 into a video signal having a television format. The display 20 generates a sectional image of the examined body in accordance with the video signal outputted from the scan converter 19.

A manual switch (not shown) movable among a predetermined number of different positions is connected to the controller 14. The controller 14 determines the positions of the switches 15, 16, and 18 in accordance with the position of the manual switch. Therefore, the selection of the generators 13a and 13b, the selection of the transducers 1a and 1b, and the selection of the processors 17a and 17b are controlled in accordance with the position of the manual switch. The selections are divided into the following eight different combinations.

When the manual switch assumes a first position, the first generator 13a, the first transducer 1a, and the first processor 17a are selected. When the manual switch assumes a second position, the first generator 13a, the first transducer 1a, and the second processor 17b are selected. When the manual switch assumes a third position, the first generator 13a, the second transducer 1b, and the first processor 17a are selected. When the manual switch assumes a fourth position, the first generator 13a, the second transducer 1b, and the second processor 17b are selected. When the manual switch assumes a fifth position, the second generator 13b, the first transducer 1a, and the first processor 17a are selected. When the manual switch assumes a sixth position, the second generator 13b, the first transducer 1a, and the second processor 17b are selected. When the manual switch assumes a seventh position, the second generator 13b, the second transducer 1b, and the first processor 17a are selected. When the manual switch assumes an eight position, the second generator 13b, the second transducer 1b, and the second processor 17b are selected.

It is preferable that the frequency characteristics of the selected signal processor match to the center frequency of the selected transducer. Accordingly, only the following four combinations among the previously-mentioned eight combinations are preferably used. In a first combination, the first generator 13a, the first transducer 1a, and the first processor 17a are selected. In a second combination, the first generator 13a, the second transducer 1b, and the second processor 17b are selected. In a third combination, the second generator 13b, the first transducer 1a, and the first processor 17a are selected. In a fourth combination, the second generator 13b, the second transducer 1b, and the second processor 17b are selected.

Figure 2:
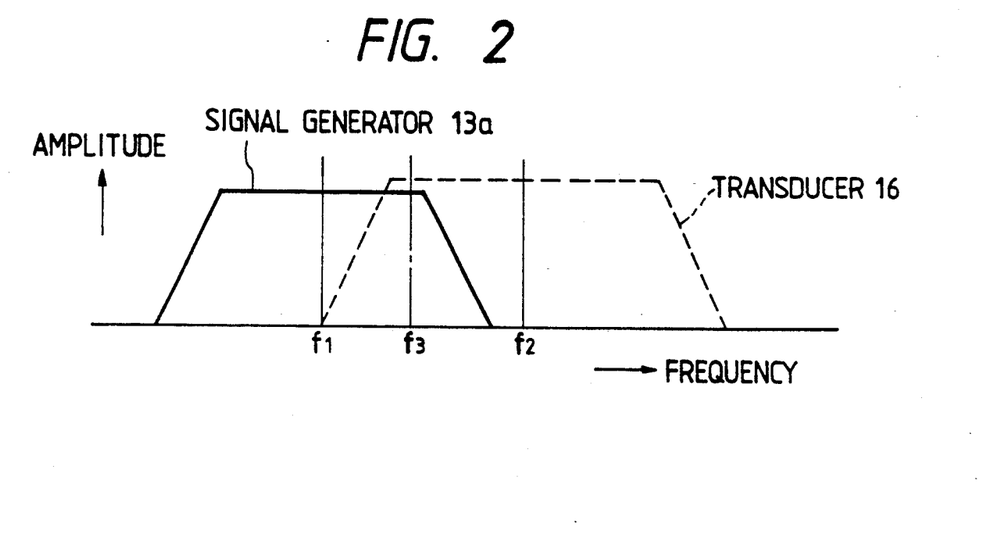
FIG. 2 is a diagram showing the frequency spectrum of the output signal from the first generator and the frequency characteristics of the second piezoelectric transducer in the apparatus of FIG. 1.

FIG. 2 shows frequency characteristics of the second combination where the first generator 13a, the second transducer 1b, and the second processor 17b are selected. As shown in FIG. 2, the first transmission signal generated by the first generator 13a has a frequency band whose center equals a frequency f1 (5 MHz). The second transducer 1b has a resonance frequency band whose center equals a frequency f2 (7.5 MHz) higher than the frequency f1. The frequency band of the first transmission signal and the resonance frequency band of the second transducer 1b partially overlap each other. In the second combination, an available sectional image of the examined body is derived from the received signals having a frequency band whose center equals a frequency f3 (6 MHz) between the frequencies f1 (5 MHz) and f2 (7.5 MHz).

Similarly, in the third combination where the second generator 13b, the first transducer 1a, and the first processor 17a are selected, an available sectional image of the examined body is derived from the received signals having a frequency band whose center equals a frequency (6.5 MHz) between the center (7.5 MHz) of the frequency band of the second transmission signal and the center (5 MHz) of the resonance frequency band of the first transducer 1a.

In the first combination where the first generator 13a, the first transducer 1a, and the first processor 17a are selected, an available sectional image of the examined body is derived from the received signals having a frequency band whose center equals the center (5 MHz) of the frequency band of the first transmission signal and the center (5 MHz) of the resonance frequency band of the first transducer 1a.

In the fourth combination where the second generator 13b, the second transducer 1b, and the second processor 17b are selected, an available sectional image of the examined body is derived from the received signals having a frequency band whose center equals the center (7.5 MHz) of the frequency band of the second transmission signal and the center (7.5 MHz) of the resonance frequency band of the second transducer 1b.

In this way, four sectional images of the examined body are obtained from the ultrasonic waves having four different frequency bands respectively by changing the combination of the used generator, the used transducer, and the used processor. The second and third combinations derive sectional images of the examined body from the ultrasonic waves in the frequency band whose center resides between the centers of the frequency bands of the first and second transmission signals. In view of the frequency-dependent attenuation of ultrasonic waves in the examined body, the second combination is more preferable than the third combination.

As understood from the previous description, a plurality of sectional images of the examined body are obtained respectively from ultrasonic waves having different frequency bands without opening a portion of the ultrasonic probe casing 3 to replace the piezoelectric transducers 1a and 1b.

This embodiment may be modified in various ways as follows. In a first modification, the rotor 90 is swung during the generation of a sectional image of an examined body. In a second modification, the transducers 1a and 1b are moved linearly during the generation of a sectional image of an examined body. In a third modification, the transducers 1a and 1b are moved along a predetermined curved line during the generation of a sectional image of an examined body. In a fourth modification, the number of the transducers, the number of the generators, and the number of the processors are three or more. A fifth modification has a single transducer.

DESCRIPTION OF THE SECOND PREFERRED EMBODIMENT

Figure 3:
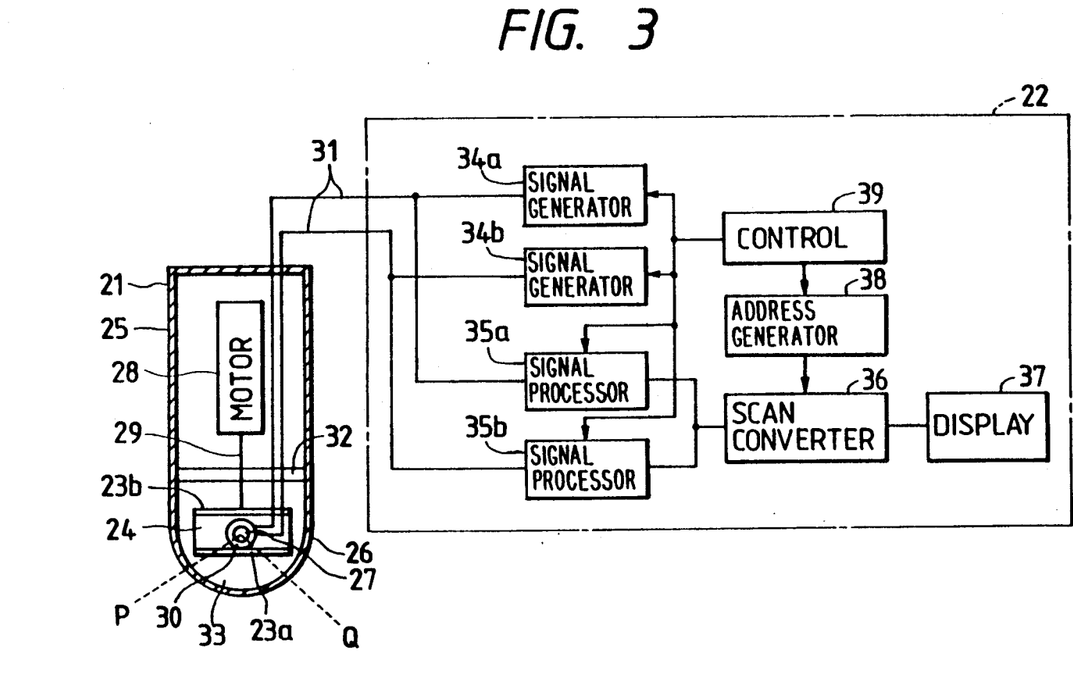
FIG. 3 is a diagram of an ultrasonic diagnostic apparatus according to a second embodiment of this invention.

With reference to FIG. 3, an ultrasonic diagnostic apparatus includes an ultrasonic probe 21 and a main body 22. The ultrasonic probe 21 is of a mechanical-scan type. As will be described hereinafter, the ultrasonic probe 21 is electrically connected to the main body 22.

For example, the ultrasonic probe 21 is designed for use in a colon of an examined body. The ultrasonic probe 21 includes first and second piezoelectric transducers 23a and 23b mounted on opposite surfaces of a rotor 24 respectively. The transducers 23a and 23b have different resonance frequency bands respectively. For example, the centers of the resonance frequency bands of the transducers 23a and 23b are 5 MHz and 7.5 MHz respectively.

The ultrasonic probe 21 has a casing 25 provided with a hemispherical front end which is made of synthetic resin and which forms an acoustic window 26. The rotor 24 is rotatably supported within the acoustic window 26 by a rotary shaft 27. As the rotor 24 rotates, the transducers 23a and 23b are sequentially opposed to the examined body.

The rotor 24 is mechanically coupled via a drive shaft 29 to a motor 28 supported within a rear part of the casing 25. The rotor 24 is driven by the motor 28. The motor 28 includes an encoder.

A partition wall provided with an oil seal 32 divides the interior of the casing 25 into a front portion and a rear portion accommodating the rotor 24 and the motor 28 respectively. The front portion of the casing 25 is sealing filled with ultrasonic wave propagation liquid 33 such as water or oil.

The main body 22 feeds and receives a transmission signal and a reception signal to and from the transducers 23a and 23b via a rotary transformer 30 and signal lines 31. The rotary transformer 30 is supported on the rotor 24 and surrounds the rotary shaft 27. The signal lines 31 extend between the rotary transformer 30 and the main body 22.

The encoder within the motor 28 is directly coupled to the drive shaft 29 and generates a signal representing conditions of rotation of the motor 28 and thus representing the positions of the rotor 24 and the transducers 23a and 23b. The output signal from the encoder is transmitted to the main body 22. The main body 22 uses the encoder signal in various controls including control of timings of the transmission and reception of ultrasonic wave.

It should be noted that a drive line to the motor 28, an output line from the encoder within the motor 28, and a power supply line to the encoder are omitted from FIG. 3 for clarity.

The main body 22 includes a transmitter having first and second signal generators 34a and 34b. The first generator 34a outputs a first transmission signal having a frequency band whose center equals 5 MHz. The second generator 13b outputs a second transmission signal having a frequency band whose center equals 7.5 MHz. The first and second transmission signals are fed from the generators 34a and 34b to the transducers 23a and 23b respectively via the signal lines 31 and the rotary transformer 30.

The main body 22 also includes a receiver having first and second signal processors 35a and 35b. The first processor 35a is able to process an echo or reception signal having a frequency band whose center equals 5 MHz. In other words, the first processor 35a has frequency characteristics matching to a frequency band whose center equals 5 MHz. The second processor 35b is able to process an echo or reception signal having a frequency band whose center equals 7.5 MHz. In other words, the second processor 35b has frequency characteristics matching to a frequency band whose center equals 7.5 MHz. Each of the processors 35a and 35b includes amplifiers, a detector, and various filters in a known way. Echo signals or received signals are transmitted from the transducers 23a and 23b to the processors 35a and 35b respectively via the rotary transformer 30 and the signal lines 31.

The transducers 23a and 23b convert the first and second transmission signals into beams of corresponding ultrasonic waves emitted into the examined body. Portions of the emitted ultrasonic beams are reflected within the examined body and return to the transducers 23a and 23b as ultrasonic echoes. The transducers 23a and 23b convert the ultrasonic echoes into received signals which are transmitted to the respective processors 35a and 35b via the rotary transformer 30 and the signal lines 31.

Output signals from the processors 35a and 35b are converted by a scan converter 36 into corresponding digital signals. The scan converter 36 includes a frame memory into which the digital signals are stored. Specifically, the digital signals are stored into storage locations of the frame memory which are designated by a write address signal outputted from an address generator 38. In the scan converter 36, the digital signals are sequentially read out from the storage locations of the frame memory and are then converted into a video signal having a television format. The storage locations of the frame memory from which the digital signals are read out are designated by a read address signal outputted from the address generator 38. A display 37 generates a sectional image of the examined body in accordance with the video signal outputted from the scan converter 36.

One of the generators 34a and 34b is selected by a control signal outputted from a controller 39. Specifically, one of the generators 34a and 34b is activated and the other is deactivated by the control signal. Similarly, one of the processors 35a and 35b is selected by the control signal outputted from the controller 39. Specifically, one of the processors 35a and 35b is activated and the other is deactivated by the control signal. The selection of the generators 34a and 34b has the following relationship with the selection of the processors 35a and 35b. When the first generator 34a is selected, the first processor 35a is selected. In this case, the first transducer 23a is used in the operation of the ultrasonic diagnostic apparatus. When the second generator 34b is selected, the second processor 35b is selected. In this case, the second transducer 23b is used in the operation of the ultrasonic diagnostic apparatus. The address signals outputted from the address generator 38 are generated in accordance with a control signal outputted from the controller 39.

The ultrasonic diagnostic apparatus operates as follows. The motor 28 drives the rotor 24 via the drive shaft 29. Specifically, the rotor 24 with the transducers 23a and 23b are rotated in one direction at a predetermined speed, for example, 1200 rpm.

During a first period, the controller 39 selects the first generator 34a and the first processor 35a so that the first devices 34a and 35a and the first transducer 23a are used in the operation of the ultrasonic diagnostic apparatus. During the first period, the first transducer 23a emits an ultrasonic wave beam into an examined body and receives echoes of the ultrasonic wave beam while the first transducer 23a is rotated through an angular range from a predetermined position P to a predetermined position Q. In this case, the ultrasonic wave beam has a frequency band whose center equals 5 MHz. The first transducer 23a converts the received echoes of the ultrasonic wave beam into a received signal which is processed by the first processor 35a. The scan converter 36 converts the output signal from the first processor 35a into a corresponding digital signal. The digital signal is stored into a storage location of the frame memory within the scan converter 36 in accordance with the write address signal from the address generator 38. The digital signal is read out from the frame memory in accordance with the read address signal from the address generator 38 and is converted by the scan converter 36 into a corresponding video signal. The display 37 indicates a sectional image of the examined body in accordance with the video signal. In this case, the sectional image of the examined body is derived from the echoes of the ultrasonic wave beam having a frequency band whose center equals 5 MHz.

During a second period between the moment of the movement of the first transducer 23a out of the position Q and the moment of the movement of the second transducer 23b into the position P, the controller 39 changes the selection of the generators 34a and 34b and the selection of the processors 35a and 35b so that the second devices 34b and 35b are moved into operable states. The controller 39 is informed of the positions of the rotor 24 and the transducers 23a and 23b by the output signal from the encoder within the motor 28. The controller 39 determines the timings of the changes of the generators 34a and 34b and the processors 35a and 35b in accordance with the output signal from the encoder.

During a third period following the second period, the controller 39 selects the second generator 34b and the second processor 35b so that the second devices 34b and 35b and the second transducer 23b are used in the operation of the ultrasonic diagnostic apparatus. During the third period, the second transducer 23b emits an ultrasonic wave beam into the examined body and receives echoes of the ultrasonic wave beam while the second transducer 23b is rotated through the angular range from the position P to the position Q. In this case, the ultrasonic wave beam has a frequency band whose center equals 7.5 MHz. The second transducer 23b converts the received echoes of the ultrasonic wave beam into a received signal which is processed by the second processor 35b. The scan converter 36 converts the output signal from the second processor 35b into a corresponding digital signal. The digital signal is stored into a storage location of the frame memory within the scan converter 36 in accordance with the write address signal from the address generator 38. The digital signal is read out from the frame memory in accordance with the read address signal from the address generator 38 and is converted by the scan converter 36 into a corresponding video signal. The display 37 indicates a sectional image of the examined body in accordance with the video signal. In this case, the sectional image of the examined body is derived from the echoes of the ultrasonic wave beam having a frequency band whose center equals 7.5 MHz.

During a fourth period between the moment of the movement of the second transducer 23b out of the position Q and the movement of the movement of the first transducer 23a into the position P, the controller 39 changes the selection of the generators 34a and 34b and the selection of the processors 35a and 35b so that the first devices 34a and 35a are moved into operable states. The controller 39 determines the timings of the changes of the generators 34a and 34b and the processors 35a and 35b in accordance with the output signal from the encoder within the motor 28 as in the second period.

It should be noted that the digital signals corresponding to the echo signals received via the transducers 23a and 23b are stored into different regions of the frame memory within the scan converter 36 respectively.

As the rotor 24 rotates through 360°, the previously-mentioned operations during the first period to the fourth period are sequentially performed and one operation cycle is completed. One operation cycle is performed for every one revolution of the rotor 24.

Figure 4:
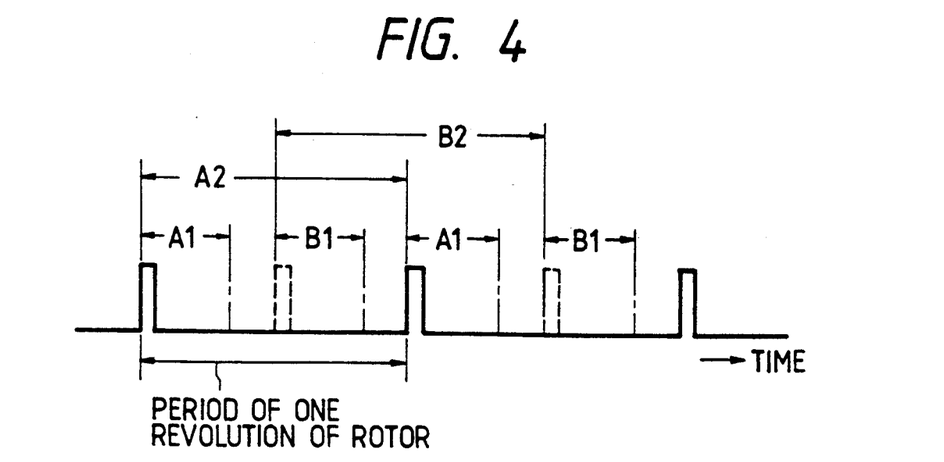
FIG. 4 is a timing chart showing the operation of the apparatus of FIG. 3.

In FIG. 4, the character A1 denotes a scanning period where the first transducer 23a moves from the position P to the position Q. The character B1 denotes a scanning period where the second transducer 23b moves from the position P to the position Q. As shown in FIG. 4, the scanning periods A1 and B1 alternate with each other. A frame period A2 includes a pair of adjacent scanning periods A1 and B1. A frame period B2 includes a pair of adjacent scanning periods B1 and A1. Each of the frame periods A2 and B2 corresponds to a period of updating of one frame having a pair of 5-MHz and 7.5-MHz sectional images. Each of the frame periods A2 and B2 corresponds to one revolution of the rotor 24. Since the rotor 24 rotates at a speed of 1200 rpm, the frame frequency equals 20 Hz.

Figure 5:
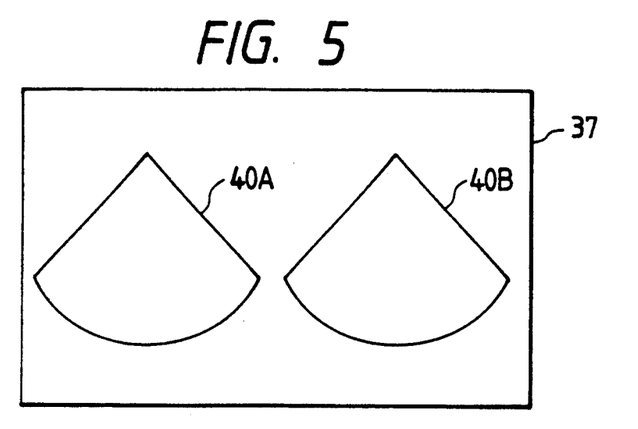
FIG. 5 is a front view of the display in the apparatus of FIG. 3.

As shown in FIG. 5, the display 37 indicates sector sectional images 40A and 40B of the examined body in separate parallel regions respectively. The sector sectional images 40A and 40B are obtained via the transducers 23a and 23b respectively. The sector sectional images 40A and 40B have a frame frequency of 20 Hz and are indicated in real time. It should be noted that only one of the sector sectional images 40A and 40B may be indicated over an entire region of the display 37.

As understood from the previous description, a plurality of sectional images of the examined body are obtained respectively from ultrasonic waves having different frequency bands without opening a portion of the ultrasonic probe casing 25 to replace the piezoelectric transducers 23a and 23b.

This embodiment may be modified in various ways as follows. In a first modification, the number of different frequency transducers is other than two. In a second modification, transducers have a common resonance frequency characteristics. In a third modification, transducers have different opening diameters or different opening shapes. In a fourth modification, transducers have different focal distances.

DESCRIPTION OF THE THIRD PREFERRED EMBODIMENT

Figure 6:
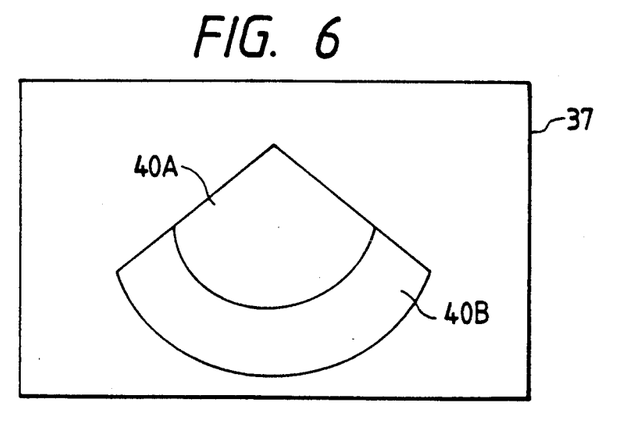
FIG. 6 is a front view of a display in an ultrasonic diagnostic apparatus according to a third embodiment of this invention.

FIG. 6 shows a third embodiment of this invention which is similar to the embodiment of FIGS. 3–5 except for the following design changes. In the embodiment of FIG. 6, the display 37 indicates 5-MHz and 7.5 sectional images 40A and 40B in a sector region. Specifically, the 5-MHz sectional image 40A occupies an inner portion of the sector region while the 7.5-MHz sectional image 40B occupies an outer portion of the sector region.

In respect of the scan converter 36 (see FIG. 3), the locations of the segments of the frame memory into which the digital signals are written are chosen so as to realize the image display manner of FIG. 6.

DESCRIPTION OF THE FOURTH PREFERRED EMBODIMENT

Figure 7:
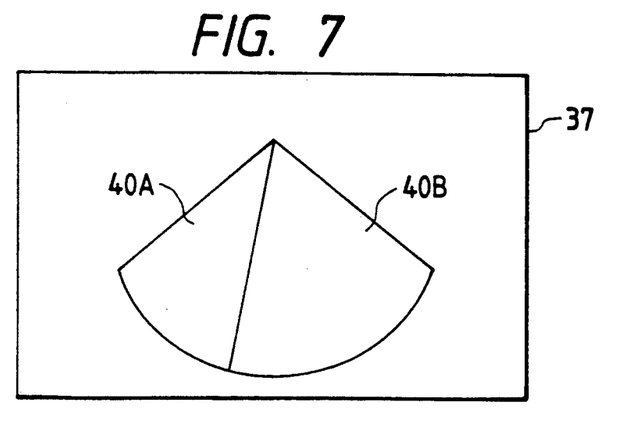
FIG. 7 is a front view of a display in an ultrasonic diagnostic apparatus according to a fourth embodiment of this invention.

FIG. 7 shows a fourth embodiment of this invention which is similar to the embodiment of FIGS. 3–5 except for the following design changes. In the embodiment of FIG. 7, the display 37 indicates 5-MHz and 7.5-MHz sectional images 40A and 40B in respective adjoining regions.

In respect of the scan converter 36 (see FIG. 3), the locations of the segments of the frame memory into which the digital signals are written are chosen so as to realize the image display manner of FIG. 7.

What is claimed is:

1. An ultrasonic diagnostic apparatus comprising:
at least one piezoelectric transducer;
means for moving the transducer in a scanning process;
means for generating a first transmission signal;
means for generating a second transmission signal different from the first transmission signal;
means for selectively applying one of the first and second transmission signals to the transducer, wherein the transducer converts the applied one of the first and second transmission signals into a beam of corresponding ultrasonic wave, wherein the transducer emits the ultrasonic wave beam toward an examined body and receives an echo of the ultrasonic wave beam from the examined body, wherein the transducer converts the received echo into a corresponding received signal;
a first signal processor having a characteristic;
a second signal processor having a characteristic different from the characteristic of the first signal processor;
means for selectively applying the received signal to one of the first and second signal processors to allow said one of the first and second signal processors to process the received signal; and
means for generating a sectional image of the examined body on the basis of an output signal from said one of the first and second signal processors.

2. The apparatus of claim 1 wherein the first transmission signal has a first frequency band and the second transmission signal has a second frequency band. centers of the first and second frequency bands are different from each other, the first signal processor has a first frequency characteristic, the second signal processor has a second frequency characteristic, and the first and second frequency characteristics are different from each other.

3. The apparatus of claim 2 wherein the transducer has a resonance frequency band whose center is higher than a center of one of the frequency bands of the first and second transmission signals.

4. An ultrasonic diagnostic apparatus comprising:
a first piezoelectric transducer having a first physical characteristic;
a second piezoelectric transducer having a second physical characteristic different from said first physical characteristic;
means for moving said transducers in a scanning process;
means for generating a first transmission signal;
means for generating a second transmission signal different from the first transmission signal;
means for selectively applying said first and second transmission signals to said transducers, wherein said transducers convert the applied said first and second transmission signals into beams of corresponding ultrasonic waves, wherein said transducers emit the ultrasonic wave beams toward an examined body and receive echoes of the ultrasonic wave beams from the examined body, wherein said transducers convert the received echoes into corresponding received signals;
a first signal processor having a characteristic;
a second signal processor having a characteristic different from the characteristic of the first signal processor;
means for selectively applying the received signals to said first and second signal processors to allow said first and second signal processors to process the received signals;
means for generating a sectional image of the examined body on the basis of output signals from said first and second signal processors; and
means for simultaneously indicating real-time sectional images of the examined body which are generated on the basis of received signals outputted from said first and second transducers respectively.

5. The apparatus of claim 4 wherein the sectional images are indicated in a format dependent on a difference between the physical characteristics of the first and second transducers.

6. The apparatus of claim 4 wherein the first piezoelectric tranducer has a resonance frequency band, the second piezoelectric transducer has a resonance frequency band, and centers of the resonance frequency bands of the first and second transducers are different from each other.

7. An ultrasonic diagnostic apparatus comprising:
a first piezoelectric transducer having a first frequency characteristic;
a second piezoelectric transducer having a second frequency characteristic different from said first frequency characteristic;
means for moving said transducers in a scanning process;
means for generating a first transmission signal;
means for generating a second transmission signal different from the first transmission signal;
means for selectively applying said first and second transmission signals to said transducers, wherein said transducers convert the applied said first and second transmission signals into beams of corresponding ultrasonic waves, wherein said transducers emit the ultrasonic wave beams toward an examined body and receive echoes of the ultrasonic wave beams from the examined body, wherein said transducers convert the received echoes into corresponding received signals;

a first signal processor having a frequency characteristic matching the first frequency characteristic of said first transducer;

a second signal processor having a frequency characteristic matching the second frequency characteristic said second transducer;

means for selectively applying received signals from the first and second transducers to the first and second signal processors respectively; and means for generating a sectional image of the examined body on the basis of output signals from said first and second signal processors.

* * * * *